(12) United States Patent
Hart (10) Patent No.: US 11,389,627 B1
(45) Date of Patent: Jul. 19, 2022

(54) BALLOON PROTECTORS, BALLOON-CATHETER ASSEMBLIES, AND METHODS THEREOF

(71) Applicant: Lutonix, Inc., New Hope, MN (US)

(72) Inventor: Colin P. Hart, Queensbury, NY (US)

(73) Assignee: Lutonix Inc., New Hope, MN (US)

( * ) Notice: Subject to any disclaimer, the term of this patent is extended or adjusted under 35 U.S.C. 154(b) by 136 days.

(21) Appl. No.: 16/150,131

(22) Filed: Oct. 2, 2018

(51) Int. Cl.
*A61M 25/10* (2013.01)

(52) U.S. Cl.
CPC .......... *A61M 25/10* (2013.01); *A61M 25/1002* (2013.01); *A61M 2025/105* (2013.01); *A61M 2025/1081* (2013.01)

(58) Field of Classification Search
CPC ...... A61M 2025/1081; A61M 25/0668; A61M 25/01; A61M 25/10; A61M 25/1002; A61M 25/1029; A61M 25/1036; A61M 25/104; A61M 25/1004; A61M 25/105; A61M 25/1081; A61M 2025/105; A61M 25/002; A61M 2025/1043; A61M 2205/0238; A61M 2209/06; A61F 2/97; A61B 50/30

See application file for complete search history.

(56) References Cited

U.S. PATENT DOCUMENTS

| | | | |
|---|---|---|---|
| 4,306,562 A | 12/1981 | Osborne |
| 4,473,067 A | 9/1984 | Schiff |
| 4,649,922 A | 3/1987 | Wiktor |
| 4,921,479 A | 5/1990 | Grayzel |
| 5,015,231 A | 5/1991 | Keith et al. |
| 5,125,904 A | 6/1992 | Lee |
| 5,147,302 A | 9/1992 | Euteneuer et al. |
| 5,158,545 A | 10/1992 | Trudell et al. |
| 5,167,634 A | 12/1992 | Corrigan, Jr. et al. |
| 5,176,698 A | 1/1993 | Burns et al. |
| 5,211,654 A | 5/1993 | Kaltenbach |

(Continued)

FOREIGN PATENT DOCUMENTS

| | | |
|---|---|---|
| AU | 2014262160 B2 | 12/2018 |
| JP | 2000-516502 A | 12/2000 |

(Continued)

OTHER PUBLICATIONS

AU 2014262160 filed Nov. 19, 2015 Office Action dated Jul. 17, 2018.

(Continued)

*Primary Examiner* — Shefali D Patel (74) *Attorney, Agent, or Firm* — Rutan & Tucker LLP (57) ABSTRACT

A balloon protector is disclosed for use with a balloon catheter including a shaft and a drug-coated balloon. The balloon protector includes a balloon-covering section configured to cover the drug-coated balloon with a running clearance fit, and a shaft-covering section coupled to the balloon-covering section. The shaft-covering section is configured to contact at least a portion of the shaft in a sliding or location clearance fit. The shaft-covering section is configured to separate from the shaft without separating from the balloon-covering section to permit translation of the balloon-covering section from a first position over the drug-coated balloon to a second position over the shaft-covering section. A catheter assembly with the balloon protector and methods of use are also disclosed.

16 Claims, 8 Drawing Sheets

(56) References Cited

U.S. PATENT DOCUMENTS

| | | |
|---|---|---|
| 5,221,263 A | 6/1993 | Sinko et al. |
| 5,222,970 A | 6/1993 | Reeves |
| 5,342,307 A | 8/1994 | Euteneuer et al. |
| 5,352,236 A | 10/1994 | Jung et al. |
| 5,366,442 A | 11/1994 | Wang et al. |
| 5,425,710 A | 6/1995 | Khair et al. |
| 5,445,645 A | 8/1995 | Debbas |
| 5,454,790 A | 10/1995 | Dubrul |
| 5,458,639 A | 10/1995 | Tsukashima et al. |
| 5,484,409 A | 1/1996 | Atkinson et al. |
| 5,496,345 A | 3/1996 | Kieturakis et al. |
| 5,499,975 A | 3/1996 | Cope et al. |
| 5,522,818 A | 6/1996 | Keith et al. |
| 5,569,294 A | 10/1996 | Parkola |
| 5,584,852 A | 12/1996 | Parkola |
| 5,591,226 A | 1/1997 | Trerotola et al. |
| 5,647,857 A | 7/1997 | Anderson et al. |
| 5,702,410 A | 12/1997 | Klunder et al. |
| 5,765,682 A | 6/1998 | Bley et al. |
| 5,766,203 A | 6/1998 | Imran et al. |
| 5,800,517 A | 9/1998 | Anderson et al. |
| 5,824,041 A | 10/1998 | Lenker et al. |
| 5,868,707 A | 2/1999 | Williams et al. |
| 5,868,719 A | 2/1999 | Tsukernik |
| 5,873,880 A | 2/1999 | Williams et al. |
| 5,893,868 A | 4/1999 | Hanson et al. |
| 5,964,730 A | 10/1999 | Williams et al. |
| 6,110,146 A | 8/2000 | Berthiaume et al. |
| 6,113,607 A | 9/2000 | Lau et al. |
| 6,132,450 A | 10/2000 | Hanson et al. |
| 6,143,016 A * | 11/2000 | Bleam .............. A61F 2/958 604/104 |
| 6,152,944 A | 11/2000 | Holman et al. |
| 6,251,119 B1 | 6/2001 | Addis |
| 6,283,743 B1 | 9/2001 | Traxler et al. |
| 6,416,529 B1 | 7/2002 | Holman et al. |
| 6,432,121 B1 | 8/2002 | Jervis |
| 6,447,540 B1 | 9/2002 | Fontaine et al. |
| 6,454,744 B1 | 9/2002 | Spohn et al. |
| 6,530,881 B1 | 3/2003 | Ailinger et al. |
| 6,533,806 B1 | 3/2003 | Sullivan et al. |
| 6,562,049 B1 | 5/2003 | Norlander et al. |
| 6,569,182 B1 | 5/2003 | Balceta et al. |
| 6,592,602 B1 | 7/2003 | Peartree et al. |
| 6,613,067 B1 | 9/2003 | Johnson |
| 6,663,595 B2 | 12/2003 | Spohn et al. |
| 6,749,584 B2 | 6/2004 | Briggs et al. |
| 6,749,601 B2 | 6/2004 | Chin |
| 6,758,854 B1 | 7/2004 | Butler et al. |
| 6,783,542 B2 | 8/2004 | Eidenschink |
| 6,790,224 B2 | 9/2004 | Gerberding |
| 6,899,727 B2 | 5/2005 | Armstrong et al. |
| 6,939,327 B2 | 9/2005 | Hall et al. |
| 6,991,639 B2 | 1/2006 | Holman et al. |
| 7,105,013 B2 | 9/2006 | Durcan |
| 7,144,386 B2 | 12/2006 | Korkor et al. |
| 7,198,636 B2 | 4/2007 | Cully et al. |
| 7,468,070 B2 | 12/2008 | Henry et al. |
| 7,497,844 B2 | 3/2009 | Spear et al. |
| 7,618,398 B2 | 11/2009 | Holman et al. |
| 7,632,256 B2 | 12/2009 | Mosler et al. |
| 7,744,571 B2 | 6/2010 | Fisher et al. |
| 7,770,726 B2 | 8/2010 | Murray et al. |
| 7,837,671 B2 | 11/2010 | Eversull et al. |
| 7,909,798 B2 | 3/2011 | Osypka |
| 7,967,798 B2 | 6/2011 | Reydel et al. |
| 7,993,305 B2 | 8/2011 | Ye et al. |
| 7,998,184 B2 | 8/2011 | Eidenschink |
| 8,025,691 B2 | 9/2011 | Carter et al. |
| 8,105,287 B2 | 1/2012 | Fisher et al. |
| 8,126,570 B2 | 2/2012 | Manning et al. |
| 8,202,309 B2 | 6/2012 | Styrc |
| 8,273,059 B2 | 9/2012 | Nardeo et al. |
| 8,292,939 B2 | 10/2012 | Yachia et al. |
| 8,308,789 B2 | 11/2012 | Armstrong |
| 8,356,457 B2 | 1/2013 | Murray et al. |
| 8,359,721 B2 | 1/2013 | Melsheimer et al. |
| 8,382,715 B2 | 2/2013 | Nardeo et al. |
| 8,444,686 B2 | 5/2013 | Holman et al. |
| 8,641,752 B1 | 2/2014 | Holm et al. |
| 8,657,789 B2 | 2/2014 | Guo et al. |
| 8,657,866 B2 | 2/2014 | Melsheimer et al. |
| 8,827,958 B2 | 9/2014 | Bierman et al. |
| 8,845,712 B2 | 9/2014 | Irwin et al. |
| 8,852,257 B2 | 10/2014 | Liu et al. |
| 8,858,614 B2 | 10/2014 | Headley, Jr. et al. |
| 8,889,211 B2 | 11/2014 | Owens et al. |
| 8,919,553 B2 | 12/2014 | Murray et al. |
| 8,932,262 B2 | 1/2015 | Ostfeld et al. |
| 9,011,512 B2 | 4/2015 | Drasler |
| 9,061,126 B2 | 6/2015 | Fischell et al. |
| 9,078,781 B2 | 7/2015 | Ryan et al. |
| 9,119,740 B2 | 9/2015 | Cannon et al. |
| 9,168,164 B2 | 10/2015 | Dorn et al. |
| 9,192,499 B2 | 11/2015 | Gibbons, Jr. |
| 9,211,206 B2 | 12/2015 | Pryor |
| 9,216,101 B2 | 12/2015 | State |
| 10,449,335 B2 | 10/2019 | Poker et al. |
| 2005/0245900 A1 | 11/2005 | Ash |
| 2005/0267562 A1 | 12/2005 | Jones et al. |
| 2006/0020327 A1 | 1/2006 | Lashinski et al. |
| 2006/0041277 A1 | 2/2006 | Deem et al. |
| 2006/0052749 A1 | 3/2006 | Moyer |
| 2006/0052750 A1 | 3/2006 | Lenker et al. |
| 2007/0016280 A1 | 1/2007 | Yacoby et al. |
| 2007/0066862 A1 | 3/2007 | Vaska |
| 2007/0225659 A1 | 9/2007 | Melsheimer |
| 2008/0146999 A1 | 6/2008 | Tanaka et al. |
| 2008/0208128 A1 | 8/2008 | Guo et al. |
| 2009/0018633 A1 | 1/2009 | Lindquist et al. |
| 2009/0018635 A1 | 1/2009 | Holman et al. |
| 2009/0018640 A1 | 1/2009 | State |
| 2009/0227948 A1 | 9/2009 | Chen et al. |
| 2009/0234290 A1 | 9/2009 | Fisher et al. |
| 2009/0287203 A1 * | 11/2009 | Mazzone .......... A61M 25/1038 606/21 |
| 2010/0069839 A1 | 3/2010 | Holman et al. |
| 2010/0069852 A1 | 3/2010 | Kelley |
| 2010/0100170 A1 | 4/2010 | Tan et al. |
| 2010/0228333 A1 * | 9/2010 | Drasler .................. A61L 29/14 623/1.11 |
| 2010/0249907 A1 | 9/2010 | Dorn et al. |
| 2010/0266656 A1 | 10/2010 | Johnson |
| 2010/0298839 A1 | 11/2010 | Castro |
| 2010/0312261 A1 | 12/2010 | Suzuki et al. |
| 2010/0331780 A1 | 12/2010 | Bellisario et al. |
| 2011/0184509 A1 | 7/2011 | Von Oepen et al. |
| 2011/0184510 A1 | 7/2011 | Maisano et al. |
| 2011/0208284 A1 | 8/2011 | Hofmann et al. |
| 2011/0208292 A1 | 8/2011 | Von Oepen et al. |
| 2011/0224680 A1 | 9/2011 | Barker |
| 2011/0264128 A1 | 10/2011 | Mauch et al. |
| 2011/0268781 A1 | 11/2011 | Cleek et al. |
| 2011/0301565 A1 | 12/2011 | Weber |
| 2012/0041537 A1 | 2/2012 | Parker et al. |
| 2012/0083740 A1 | 4/2012 | Chebator et al. |
| 2012/0109281 A1 | 5/2012 | Papp |
| 2012/0143138 A1 | 6/2012 | King et al. |
| 2012/0143303 A1 | 6/2012 | Dorn et al. |
| 2012/0221089 A1 | 8/2012 | Drasler |
| 2012/0277843 A1 | 11/2012 | Weber et al. |
| 2012/0296313 A1 | 11/2012 | Andreacchi et al. |
| 2012/0302955 A1 | 11/2012 | Liu et al. |
| 2012/0324696 A1 | 12/2012 | Liu et al. |
| 2013/0018309 A1 | 1/2013 | Ewing et al. |
| 2013/0030519 A1 | 1/2013 | Tran et al. |
| 2013/0090624 A1 | 4/2013 | Munsinger |
| 2013/0226276 A1 | 8/2013 | Newell et al. |
| 2013/0226279 A1 | 8/2013 | Slattery et al. |
| 2013/0253466 A1 | 9/2013 | Campbell et al. |
| 2013/0274720 A1 | 10/2013 | Brannon |
| 2013/0296877 A1 | 11/2013 | Irwin et al. |
| 2014/0052104 A1 | 2/2014 | Osada et al. |
| 2014/0066904 A1 | 3/2014 | Young |

(56) References Cited

U.S. PATENT DOCUMENTS

| | | |
|---|---|---|
| 2014/0120287 A1 | 5/2014 | Jacoby et al. |
| 2014/0142681 A1 | 5/2014 | Norris |
| 2014/0157567 A1 | 6/2014 | Wang et al. |
| 2014/0157573 A1 | 6/2014 | Guo et al. |
| 2014/0277359 A1 | 9/2014 | Slazas et al. |
| 2014/0277362 A1 | 9/2014 | Roeder |
| 2014/0324149 A1 | 10/2014 | Slattery et al. |
| 2014/0336581 A1 | 11/2014 | Collin |
| 2014/0379064 A1 | 12/2014 | Pacetti et al. |
| 2015/0025564 A1 | 1/2015 | Tsutsui et al. |
| 2015/0119922 A1 | 4/2015 | Kamel et al. |
| 2015/0126930 A1 | 5/2015 | Bierman et al. |
| 2015/0151087 A1 | 6/2015 | Suzuki et al. |
| 2015/0246210 A1 | 9/2015 | Yacoby et al. |
| 2015/0257910 A1 | 9/2015 | Duong et al. |
| 2015/0306361 A1 | 10/2015 | Feig et al. |
| 2016/0008583 A1 | 1/2016 | Guo et al. |
| 2016/0022456 A1 | 1/2016 | Butler et al. |
| 2016/0038321 A1 | 2/2016 | Shumer et al. |
| 2016/0038713 A1 | 2/2016 | Kearns et al. |
| 2016/0058983 A1* | 3/2016 | Poker ............... A61L 29/16 604/509 |
| 2016/0158513 A1 | 6/2016 | Ryu et al. |
| 2017/0312110 A1 | 11/2017 | Pacetti et al. |
| 2019/0224448 A1* | 7/2019 | Connors ......... A61M 25/1025 |

FOREIGN PATENT DOCUMENTS

| | | |
|---|---|---|
| JP | 2005-211492 A | 8/2005 |
| JP | 2012-183401 A | 9/2012 |
| JP | 3182410 U | 3/2013 |
| WO | 1995030449 A1 | 11/1995 |
| WO | 9806452 A1 | 2/1998 |
| WO | 2006053308 A2 | 5/2006 |
| WO | 2010120425 A2 | 10/2010 |
| WO | 2011075727 A1 | 6/2011 |
| WO | 2013064215 A1 | 5/2013 |
| WO | 2014072212 A2 | 5/2014 |
| WO | 2015011712 A1 | 1/2015 |

OTHER PUBLICATIONS

JP 2016-512088 filed May 2, 2014 Office Action dated Feb. 13, 2018.
JP 2016-512088 filed May 2, 2014 Office Action dated Jun. 14, 2018.
NZ 714341 filed Nov. 19, 2015 Examination Report dated Feb. 5, 2018.
NZ 714341 filed Nov. 19, 2015 Examination Report dated Jul. 24, 2018.
PCT/US2014/036693 filed May 2, 2014 International Preliminary Report and Written Opinion dated Nov. 3, 2015.
PCT/US2014/036693 filed May 2, 2014 International Preliminary Report dated Nov. 3, 2015.
U.S. Appl. No. 14/888,378, filed Oct. 30, 2015 Non-Final Office Action dated Apr. 16, 2018.
U.S. Appl. No. 14/888,378, filed Oct. 30, 2015 Non-Final Office Action dated Jun. 1, 2017.
NZ 750448 filed Feb. 5, 2019 Examination Report dated Aug. 12, 2019.
U.S. Appl. No. 14/888,378, filed Oct. 30, 2015 Advisory Action dated Mar. 8, 2018.
U.S. Appl. No. 14/888,378, filed Oct. 30, 2015 Final Office Action dated Mar. 18, 2019.
U.S. Appl. No. 14/888,378, filed Oct. 30, 2015 Final Office Action dated Nov. 22, 2017.
U.S. Appl. No. 14/888,378, filed Oct. 30, 2015 Non-Final Office Action dated Oct. 29, 2018.
U.S. Appl. No. 14/888,378, filed Oct. 30, 2015 Notice of Allowance dated Jun. 11, 2019.

* cited by examiner

See FIG. 5, Step 508.

FIG. 4C

See FIG. 5, Steps 510 and 512.

FIG. 4D

See FIG. 5, Steps 514 and 516. → FIG. 4E

BALLOON PROTECTORS, BALLOON-CATHETER ASSEMBLIES, AND METHODS THEREOF

BACKGROUND

Atherosclerosis is characterized by one or more intravascular lesions formed in part of plaque including blood-borne substances such as fat, cholesterol, and calcium. An intravascular lesion such as an arterial lesion can form on a wall of an arterial lumen and build out across the lumen to an opposite wall thereof. A last point of patency often occurs at a boundary between the arterial lesion and the opposite wall of the arterial lumen. Surgical interventions for atherosclerosis such as balloon angioplasty with drug-coated balloons can be used to restore patency and blood flow lost to the one or more intravascular lesions.

Balloon protectors are designed to cover and protect the drug-coated balloons of drug-coated balloon catheters during shipping and handling, which is needed to maintain integrity of the drug-coated balloons for surgical interventions. While the foregoing need for balloon protectors continues to exist, additional needs exist such as a need for protecting clinicians and others from inadvertently coming into contact with anti-proliferative drugs of the drug-coated balloons when handling drug-coated balloon catheters both before and after the surgical interventions. Disclosed herein are balloon protectors, balloon catheters with the balloon protectors, and methods thereof that meet or exceed the foregoing needs.

SUMMARY

Disclosed herein is a balloon protector for use with a balloon catheter. The balloon catheter includes a shaft and a drug-coated balloon. The balloon protector includes, in some embodiments, a balloon-covering section configured to cover the drug-coated balloon with a running clearance fit and a shaft-covering section coupled to the balloon-covering section. The shaft-covering section is configured to contact at least a portion of the shaft in a sliding or location clearance fit. The shaft-covering section is configured to separate from the shaft without separating from the balloon-covering section to permit translation of the balloon-covering section from a first position over the drug-coated balloon to a second position over the shaft.

In some embodiments, the balloon protector further includes a transitional section coupling the shaft-covering section to the balloon-covering section. The transitional section is configured to cover a proximal shoulder of the balloon in the first position.

In some embodiments, the balloon-covering section includes a flared section configured to cover a distal shoulder of the balloon in the first position. The flared section includes a circumferential tab configured to facilitate translation of the balloon protector relative to the balloon catheter.

In some embodiments, the shaft-covering section includes two or more pull tabs configured to facilitate separation of the shaft-covering section from the shaft.

In some embodiments, the shaft-covering section includes two or more weakened areas aligned with the two or more pull tabs. The two or more weakened areas are selected from the group consisting of perforations, scores, molded grooves, and combinations thereof.

In some embodiments, the balloon-covering section and the shaft-covering section are formed of expanded polytetrafluoroethylene or high-density polyethylene.

Also disclosed herein is a balloon protector including, in some embodiments, a balloon-covering section and a shaft-covering section of the balloon protector. The balloon-covering section of the balloon protector is configured to cover a drug-coated balloon disposed about a distal end portion of a balloon catheter with a running clearance fit over the balloon. The shaft-covering section of the balloon protector is configured to cover at least a portion of a shaft of the balloon catheter adjacent to a proximal end of the balloon with a sliding or location clearance fit over the shaft. The shaft-covering section of the balloon protector is configured to peel away from the shaft, thereby allowing the balloon-covering section of the balloon protector to slide off the balloon.

In some embodiments, the balloon protector further includes a transitional section between a smaller diameter of the shaft-covering section and a larger diameter of the balloon-covering section of the balloon protector. The transitional section of the balloon protector is configured to cover a proximal shoulder of the balloon of the balloon catheter.

In some embodiments, the balloon protector further includes a flared section of a distal end portion of the balloon protector. The flared section of the balloon protector is configured to cover a distal shoulder of the balloon of the balloon catheter. The flared section of the balloon protector is also configured to provide a circumferential tab for pulling the balloon protector over the balloon of the balloon catheter subsequent to sliding the balloon protector off the balloon.

In some embodiments, the balloon protector further includes two or more pull tabs of a proximal end portion of the balloon protector. The pull tabs are configured to provide a starting point from which to peel the shaft-covering section of the balloon protector away from the shaft of the balloon catheter.

In some embodiments, the balloon protector further includes two or more weakened areas extending along a length of the shaft-covering section of the balloon protector. The weakened areas are selected from perforations, scores, and molded grooves.

In some embodiments, the balloon protector is formed of a polymeric material in which main chains of the polymeric material are oriented along a length of the shaft-covering section of the balloon protector in an amount sufficient for peeling the shaft-covering section away from the shaft of the balloon catheter along the length of the shaft-covering section.

In some embodiments, the balloon protector is formed of expanded polytetrafluoroethylene or high-density polyethylene.

Also disclosed herein is a catheter assembly including, in some embodiments, a balloon catheter and a balloon protector. The balloon catheter includes a shaft and an anti-proliferative drug-coated balloon in an uninflated state disposed about a distal end portion of the shaft. The balloon protector includes a balloon-covering section coupled to a shaft-covering section. The balloon-covering section is configured to cover the balloon with a running clearance fit. The shaft-covering section is configured to contact at least a portion of the shaft with a sliding or location clearance fit. The shaft-covering section is configured to separate from the shaft without separating from the balloon-covering section to permit translation of the balloon-covering section from a first position over the drug-coated balloon to a second position over the shaft.

In some embodiments, the balloon protector further includes a transitional section coupling the shaft-covering section to the balloon-covering section. The transitional section is configured to cover a proximal shoulder of the balloon in the first position.

In some embodiments, the balloon-covering section includes a flared section configured to cover a distal shoulder of the balloon in the first position. The flared section includes a circumferential tab configured to facilitate translation of the balloon protector relative to the balloon catheter.

In some embodiments, the shaft-covering section includes two or more pull tabs configured to facilitate separation of the shaft-covering section from the shaft.

In some embodiments, the shaft-covering section includes two or more weakened areas aligned with the two or more pull tabs. The two or more weakened areas are selected from the group consisting of perforations, scores, molded grooves, and combinations thereof.

In some embodiments, the shaft-covering section is formed of a polymeric material in which main chains of the polymeric material are oriented along a length of the shaft-covering section in an amount sufficient for separating the shaft-covering section from the shaft.

In some embodiments, the balloon catheter further includes a bifurcated hub at a proximal end of the shaft. The bifurcated hub has an inflation port fluidly connected to the balloon by way of an inflation lumen of the shaft. The bifurcated hub also has a guide wire port connected to a guide wire lumen extending along an entire length of the shaft.

Also disclosed herein is catheter assembly including, in some embodiments, a balloon catheter and a balloon protector. The balloon catheter includes a shaft and an anti-proliferative drug-coated balloon disposed about a distal end portion of the shaft of the balloon catheter. The balloon protector includes a balloon-covering section and a shaft-covering section of the balloon protector. The balloon-covering section of the balloon protector is configured to cover the balloon of the balloon catheter with a running clearance fit over the balloon. The shaft-covering section of the balloon protector is configured to cover at least a portion of the shaft of the balloon catheter adjacent to a proximal end of the balloon with a sliding or location clearance fit over the shaft. The shaft-covering section of the balloon protector is configured to peel away from the shaft of the balloon catheter, thereby allowing the balloon-covering section of the balloon protector to slide off the balloon of the balloon catheter.

In some embodiments, the balloon protector further includes a transitional section between a smaller diameter of the shaft-covering section and a larger diameter of the balloon-covering section of the balloon protector. The transitional section of the balloon protector is configured to cover a proximal shoulder of the balloon not including the anti-proliferative drug.

In some embodiments, the balloon protector further includes a flared section of a distal end portion of the balloon protector. The flared section of the balloon protector is configured to cover a distal shoulder of the balloon of the balloon catheter, which distal shoulder of the balloon does not include the anti-proliferative drug.

In some embodiments, the flared section of the balloon protector forms a circumferential tab configured for pulling the balloon protector over the balloon of the balloon catheter subsequent to sliding the balloon protector off the balloon.

In some embodiments, the balloon protector further includes two or more pull tabs of a proximal end portion of the balloon protector. The pull tabs are configured to provide a starting point from which to peel the shaft-covering section of the balloon protector away from the shaft of the balloon catheter.

In some embodiments, the balloon protector further includes two or more weakened areas extending along a length of the shaft-covering section of the balloon protector. The weakened areas are selected from perforations, scores, and molded grooves.

In some embodiments, the balloon protector is formed of a polymeric material in which main chains of the polymeric material are oriented along a length of the shaft-covering section of the balloon protector in an amount sufficient for peeling the shaft-covering section away from the shaft of the balloon catheter along the length of the shaft-covering section.

In some embodiments, the balloon protector is formed of expanded polytetrafluoroethylene.

In some embodiments, the balloon catheter further includes a bifurcated hub 128 at a proximal end of the shaft of the balloon catheter. The bifurcated hub 128 has an inflation port fluidly connected to the balloon of the balloon catheter by way of an inflation lumen of the shaft of the balloon catheter. The bifurcated hub 128 also has a guide wire port connected to a guide wire lumen extending along an entire length of the shaft of the balloon catheter.

Also disclosed herein is a method of a catheter assembly including, in some embodiments, separating a shaft-covering section of a balloon protector from a shaft of a balloon catheter. The shaft-covering section is configured to contact at least a portion of the shaft in a sliding or location clearance fit. The method further includes translating a balloon-covering section from a first position in which the balloon-covering section has a running clearance fit over a drug-coated balloon to a second position over the shaft without separating the balloon-covering section from the shaft-covering section.

In some embodiments, separating the shaft-covering section from the shaft includes peeling the shaft-covering section in a direction toward a distal end of the balloon catheter, and translating the balloon-covering section from the first position to the second position includes sliding the balloon-covering section in a direction toward a proximal end of the balloon catheter.

In some embodiments, separating the shaft-covering section from the shaft includes peeling the shaft-covering section up to a transitional section coupling the shaft-covering section to the balloon-covering section. The transitional section is configured to cover a proximal shoulder of the balloon in the first position.

In some embodiments, separating the shaft-covering section from the shaft includes grasping two pull tabs of the shaft-covering section and pulling at least one pull tab of the two pull tabs away from the shaft.

In some embodiments, the method further includes translating the balloon-covering section from the second position to the first position, and preparing the balloon catheter for insertion into a patient. Translating the balloon-covering section from the second position to the first position protects the balloon while preparing the balloon catheter for insertion into the patient.

In some embodiments, the method further includes translating the balloon-covering section from the second position to the first position after withdrawing the balloon catheter from a patient. Translating the balloon-covering section from the second position to the first position protects clinicians and others from inadvertently coming into contact with any residual anti-proliferative drug on the balloon when handling the balloon catheter after use on the patient.

In some embodiments, translating the balloon-covering section from the second position to the first position includes pulling the balloon protector in a direction toward a distal end of the balloon catheter by a circumferential tab formed of a flared section of the balloon-covering section.

Also disclosed herein is a method of a catheter assembly including, in some embodiments, peeling a shaft-covering section of a balloon protector away from a shaft of a balloon catheter and sliding a balloon-covering section of the balloon protector off a drug-coated balloon of the balloon catheter after the shaft-covering section of the balloon protector is peeled away from the shaft of the balloon catheter. The shaft-covering section of the balloon protector has a sliding or location clearance fit over the shaft of the balloon catheter, and the balloon-covering section of the balloon protector has a running clearance fit over the balloon of the balloon catheter.

In some embodiments, peeling the shaft-covering section of the balloon protector includes peeling the shaft-covering section in a direction toward a distal end of the balloon catheter, and sliding the balloon-covering section of the balloon protector includes sliding the balloon-covering section in a direction toward a proximal end of the balloon catheter.

In some embodiments, peeling the shaft-covering section of the balloon protector includes peeling the shaft-covering section up to a transitional section of the balloon protector between a smaller diameter of the shaft-covering section and a larger diameter of the balloon-covering section of the balloon protector. The transitional section of the balloon protector is configured to cover a proximal shoulder of the balloon of the balloon protector.

In some embodiments, peeling the shaft-covering section of the balloon protector includes grasping two pull tabs of a proximal end portion of the balloon protector and pulling at least one pull tab of the two pull tabs away from the shaft of the balloon catheter.

In some embodiments, peeling the shaft-covering section of the balloon protector includes pinching two opposing proximal end portions of the balloon protector and pulling at least one proximal end portion of the two opposing proximal end portions away from the shaft of the balloon catheter.

In some embodiments, the method further includes sliding the balloon-covering section of the balloon protector back over the balloon of the balloon catheter and preparing the balloon catheter for insertion into a patient. Sliding the balloon-covering section of the balloon protector back over the balloon of the balloon catheter protects the balloon while preparing the balloon catheter for insertion into the patient.

In some embodiments, the method further includes sliding the balloon-covering section of the balloon protector back over the balloon of the balloon catheter after withdrawing the balloon catheter from a patient. Sliding the balloon-covering section of the balloon protector back over the balloon of the balloon catheter protects clinicians and others from inadvertently coming into contact with any residual anti-proliferative drug on the balloon when handling the balloon catheter after use on the patient.

In some embodiments, sliding the balloon-covering section of the balloon protector back over the balloon includes pulling the balloon protector by a circumferential tab formed of a flared section of a distal end portion of the balloon protector in a direction toward a distal end of the balloon catheter.

These and other features of the concepts provided herein will become more apparent to those of skill in the art in view of the accompanying drawings and following description, which disclose particular embodiments of such concepts in greater detail.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "front," "back," "top," "bottom," "proximal," "distal," and the like, are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Unless defined otherwise, all technical and scientific terms used herein have the same meaning as commonly understood by those of ordinary skill in the art.

Balloon protectors are designed to cover and protect the drug-coated balloons of drug-coated balloon catheters during shipping and handling, which is needed to maintain integrity of the drug-coated balloons for the surgical interventions for which they are designed. While the foregoing need for balloon protectors continues to exist, additional needs exist such as a need for protecting clinicians and others from inadvertently coming into contact with antiproliferative drugs of the drug-coated balloons when handling drug-coated balloon catheters both before and after the surgical interventions. Disclosed herein are balloon protectors, balloon catheters with the balloon protectors, and methods thereof that meet or exceed the foregoing needs. Catheter assemblies including a balloon catheter and a balloon protector will be addressed first, followed by balloon protectors, and methods of the foregoing.

Catheter Assemblies

Figure 1A:
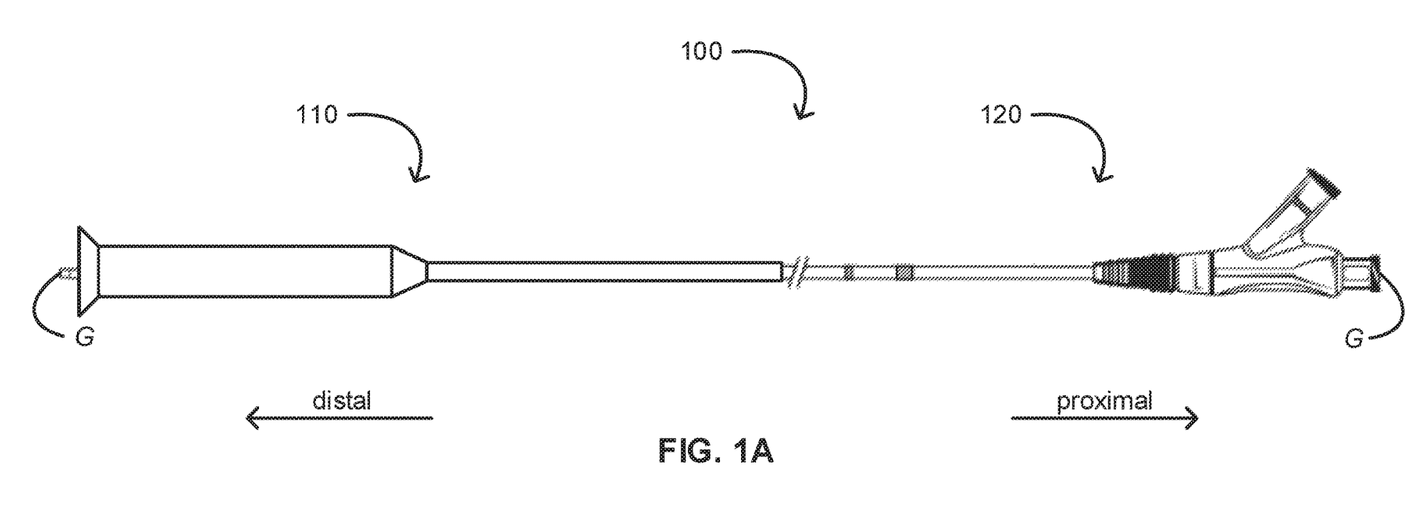
FIG. 1A illustrates a catheter assembly including a balloon protector over a balloon catheter in accordance with some embodiments.
Figure 1B:
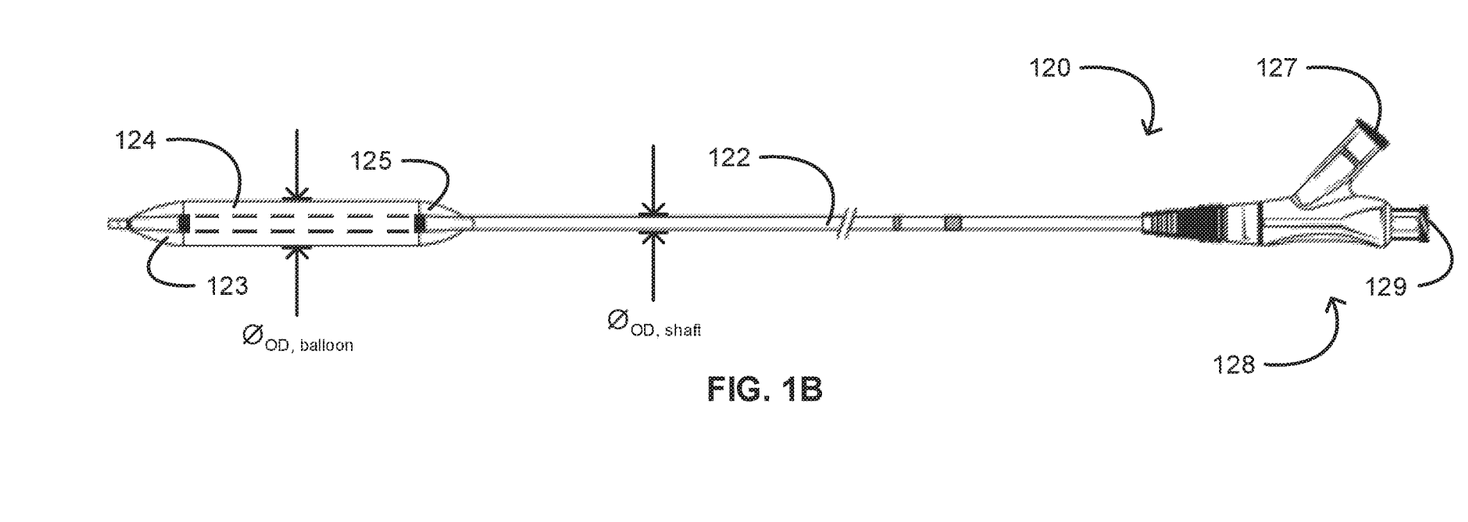
FIG. 1B illustrates the balloon catheter of FIG. 1A without the balloon protector in accordance with some embodiments.

FIG. 1A illustrates a catheter assembly 100 including a balloon protector 110 over a balloon catheter 120 in accordance with some embodiments. FIG. 1B illustrates the balloon catheter 120 of FIG. 1A without the balloon protector 110 in accordance with some embodiments.

As shown, the catheter assembly 100 includes the balloon catheter 120 and the balloon protector 110. While the catheter assembly 100 of FIGS. 1A and 1B is shown with a balloon 124 of the balloon catheter 120 in an exaggerated state to emphasize a difference in diameter from a shaft 122 of the balloon catheter 120, it should be understood that the catheter assembly 100 is typically provided with the balloon 124 in an uninflated state in which the diameter of the balloon 124 is relatively closer to that of the shaft 122.

With respect to the balloon catheter 120 of FIGS. 1A and 1B, the balloon catheter 120 includes a shaft 122 and the balloon 124 disposed about a distal end portion of the shaft 122 of the balloon catheter 120. The balloon catheter 120 further includes a bifurcated hub 128 at a proximal end of the shaft 122 of the balloon catheter 120. The bifurcated hub 128 has an inflation port 127 fluidly connected to the balloon 124 of the balloon catheter 120 by way of an inflation lumen of the shaft 122 of the balloon catheter 120. The bifurcated hub 128 also has a guide wire port 129 connected to a guide wire lumen extending along an entire length of the shaft 122 of the balloon catheter 120. FIG. 1A shows a guide wire G within the guide wire lumen of the shaft 122, wherein the guide wire enters the guide wire port 129 of the bifurcated hub 128 and exits a distal end of the shaft 122. While the guide wire G can be included in the catheter assembly 100, the guide wire G need not be included in the catheter assembly 100.

The balloon 124 of the balloon catheter 120 can be a drug-coated balloon disposed about the distal end portion of the shaft 122, wherein the drug coating the balloon 124 is an anti-proliferative or anti-restenotic drug such as paclitaxel or rapamycin. The balloon 124 includes a proximal shoulder 125 and a distal shoulder 123 of the balloon 124, between which shoulders the drug coating is typically found. That is, the proximal shoulder 125 and the distal shoulder 123 of the balloon 124 do not typically include the anti-proliferative drug. This is because the shoulders are not typically placed in apposition to an arterial-lumen wall during a surgical intervention for atherosclerosis. Notwithstanding the foregoing, the balloon 124 of the balloon catheter 120 need not include a drug coating in some embodiments.

With respect to the balloon protector 110 of FIGS. 1A and 1B, the balloon protector 110 is primarily addressed in the following section on balloon protectors, which includes making the balloon protectors. However, the balloon protector 100 is also partly addressed in making catheter assemblies such as the catheter assembly 100. Making the catheter assembly 100 includes obtaining the balloon protector 110, or a precursor thereof, and installing the balloon protector 110 over both the balloon 124 and the shaft 122 of the balloon catheter 120, or a precursor thereof, to form the catheter assembly 100.

The balloon protector 110 can have a shaft-covering section 114 with an inner diameter (see FIGS. 2A and 2C) configured for sliding the balloon protector 110 in a proximal direction, with the shaft-covering section 114 first, over the balloon 124 of the balloon catheter 120 when the balloon 124 is in an uninflated state. Making the catheter assembly 100 with such a balloon protector includes obtaining the balloon protector 110 and the balloon catheter 120, sliding the balloon protector 110 over the balloon 124 of the balloon catheter 120 when the balloon 124 is in an uninflated state, and positioning the balloon protector 110 over both the balloon 124 and the shaft 122 of the balloon catheter 120.

A precursor of the balloon protector 110 can include a heat-shrinkable tube with an inner diameter configured for sliding the heat-shrinkable tube over the balloon 124 of the balloon catheter 120 when the balloon 124 is in an uninflated state; however, the inner diameter of the heat-shrinkable tube can also be configured to accommodate the balloon 124 of the balloon catheter 120 in an inflated state. Making the catheter assembly 100 with such a precursor to the balloon protector 110 includes obtaining the heat-shrinkable tube and the balloon catheter 120, sliding the heat-shrinkable tube over the balloon 124 of the balloon catheter 120 when the balloon 124 is in an uninflated state, positioning the balloon protector 110 over both the balloon 124 and the shaft 122 of the balloon catheter 120, and heat-shrinking the heat-shrinkable tube to form the balloon protector 110 over the balloon catheter 120. The heat-shrinking of the heat-shrinkable tube can include applying heat to just a portion of the heat-shrinkable tube corresponding to the shaft-covering section 114 of the balloon protector 110, applying a sufficient amount of heat to heat-shrink the heat-shrinkable tube but an insufficient amount of heat to melt or decompose the drug coating the balloon 124 of the balloon catheter 120, or both. Alternatively, the balloon 124 does not include a drug coating, thereby obviating precautionary measures such as the foregoing to limit heat damage to drug coating the balloon 124.

A precursor of the balloon catheter 120 can include the balloon 124 disposed over the distal end portion of the shaft 122 prior to attaching the bifurcated hub 128 to form the balloon catheter 120. The shaft-covering section 114 of the balloon protector 110 can have an inner diameter (see FIGS. 2A and 2C) configured for sliding the balloon protector 110 in a distal direction, with a balloon-covering section 112 first (see FIGS. 2A and 2B), over the shaft 122 of the precursor of the balloon catheter 120. Making the catheter assembly 100 with such a precursor to the balloon catheter 120 includes obtaining the balloon protector 110 and the precursor to the balloon catheter 120, sliding the balloon protector 110 over the shaft 122 of the precursor to the balloon catheter 120, positioning the balloon protector 110 over both the balloon 124 and the shaft 122 of the precursor of the balloon catheter 120 when the balloon 124 is in an uninflated state, and attaching the bifurcated hub 128 to form the balloon catheter 120.

Balloon Protectors

Figure 2A:
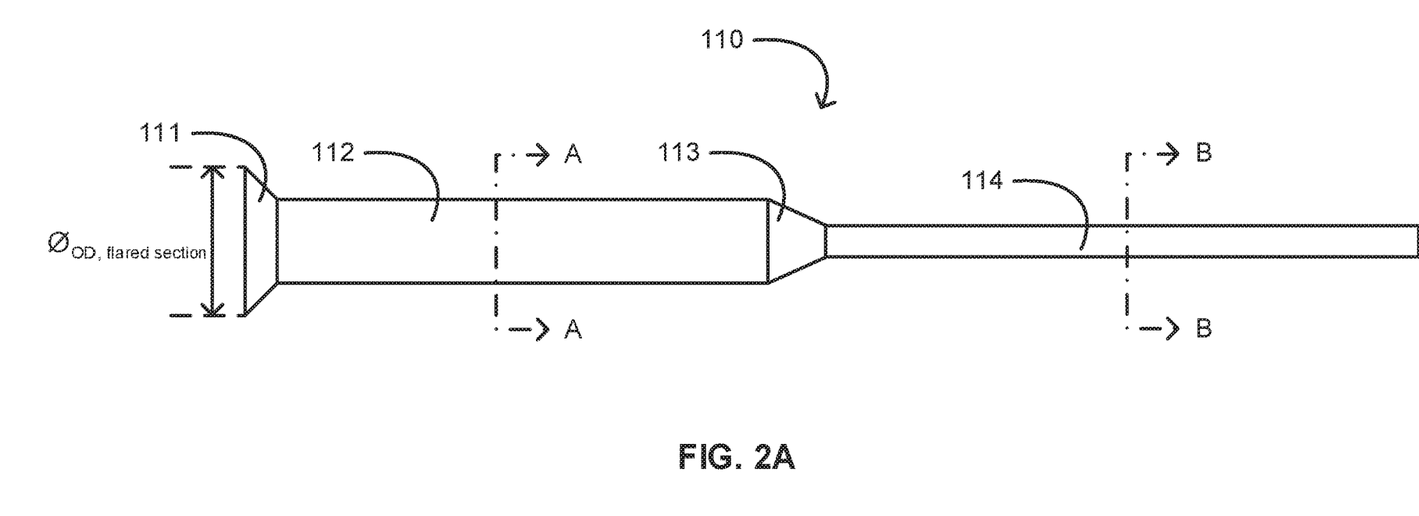
FIG. 2A illustrates a balloon protector in accordance with some embodiments.
Figure 2B:
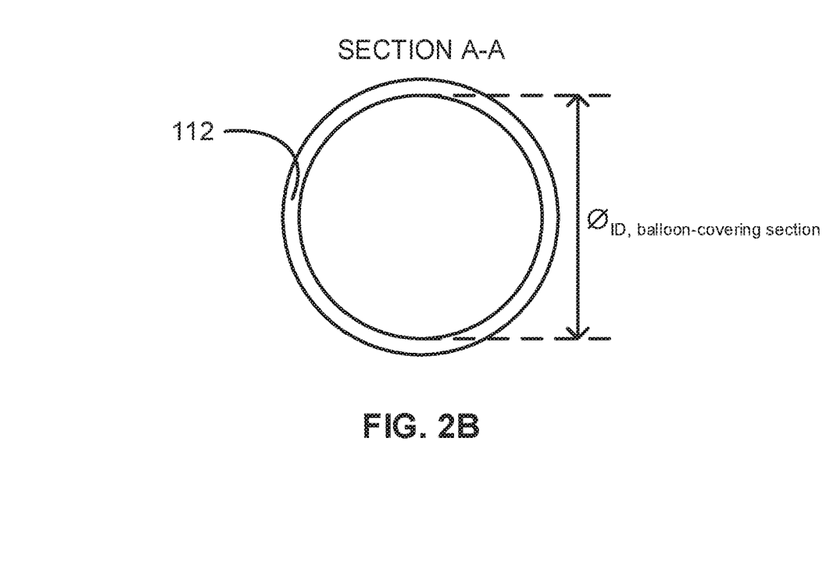
FIG. 2B illustrates a cross-section of a balloon-covering section of the balloon protector of FIG. 2A in accordance with some embodiments.
Figure 2C:
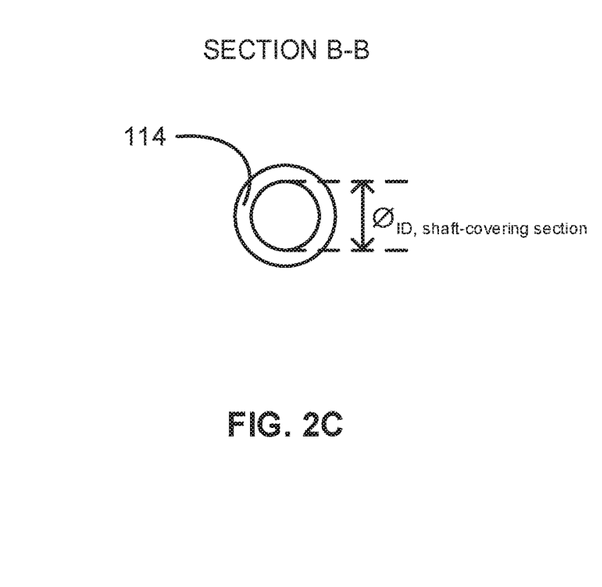
FIG. 2C illustrates a cross-section of a shaft-covering section of the balloon protector of FIG. 2A in accordance with some embodiments.

FIG. 2A illustrates the balloon protector 110 in accordance with some embodiments. FIG. 2B illustrates a cross-section of a balloon-covering section 112 of the balloon protector 110 of FIG. 2A, and FIG. 2C illustrates a cross-section of a shaft-covering section 114 of the balloon protector 110 of FIG. 2A.

As shown, the balloon protector 110 includes the balloon-covering section 112 and the shaft-covering section 114 of the balloon protector 110. The balloon-covering section 112 of the balloon protector 110 is configured to cover the balloon 124 disposed about the distal end portion of the shaft 122 of the balloon catheter 120 with a running clearance fit over the balloon 124. That is, the balloon-covering section 112 of the balloon protector 110 has an inner diameter with a running clearance fit over an outer diameter of the balloon 124 of the balloon catheter 120. When the balloon 124 is in an uninflated state, the running clearance fit can be a loose-running clearance fit or a free-running clearance fit. When the balloon 124 is in an inflated state the running clearance fit can be an easy-running clearance fit or a close-running clearance fit. (See International Organization for Standardization ["ISO"] 2768 for such tolerances.) The shaft-covering section 114 of the balloon protector 110 is configured to cover at least a portion of the shaft 122 of the balloon catheter 120 adjacent to a proximal end of the balloon 124, or the proximal shoulder 125 of the balloon 24, with a sliding or location clearance fit over the shaft 122. That is, the shaft-covering section 112 of the balloon protector 110 has an inner diameter with at least a sliding or location clearance fit up to at least a tight or similar transition fit over an outer diameter of the shaft 122 of the balloon catheter 120. (See ISO 2768 for such tolerances.) The shaft-covering section 114 of the balloon protector 110 is configured to separate or peel away from the shaft 122 of the balloon catheter 120, thereby allowing the balloon-covering section 112 of the balloon protector 110 to slide off the balloon 124 of the balloon catheter 120. (See, for example, FIGS. 4A and 4B.) That is, peeling the shaft-covering section 114 of the balloon protector 110 away from the shaft 122 of the balloon catheter 120 permits translation of the balloon-covering section 114 from a first position over the balloon 124 to a second position over the shaft 122 of the balloon catheter 120.

The balloon protector 110 further includes a transitional section 113 between a smaller diameter of the shaft-covering section 114 and a larger diameter of the balloon-covering section 112 of the balloon protector 110. The transitional section 113 of the balloon protector 110 is configured to cover the proximal shoulder 125 of the balloon 124 of the balloon catheter 120, which typically does not include an anti-proliferative drug.

The balloon protector 110 further includes a flared section 111 of a distal end portion of the balloon protector 110. The flared section 111 of the balloon protector 110 is configured to cover the distal shoulder 123 of the balloon 124 of the balloon catheter 120, which typically does not include an anti-proliferative drug. As shown, in FIG. 1A the distal end of the shaft 122 of the balloon catheter 120 can extend beyond the flared section 111 of the balloon protector 110. This is because the balloon-covering section 112 of the balloon protector 110 typically already covers a full extent of the drug coating of the balloon 124 between the proximal shoulder 125 and the distal shoulder 123 of the balloon 124, thereby obviating extension of the balloon protector 110 past the distal end of the shaft 122 of the balloon catheter 120. The flared section 111 of the balloon protector 110 is also configured to provide a circumferential tab configured for pulling the balloon protector 110 over the balloon 124 of the balloon catheter 120 subsequent to sliding the balloon protector 110 off the balloon 124. (See, for example, FIG. 4C.)

The balloon protector 110 can be of one or more polymeric materials including, but not limited to, expanded polytetrafluoroethylene ("ePTFE") or high-density polyethylene ("HDPE"). When the balloon protector 110 is molded from the one or more polymeric materials, the molded balloon protector 110 is characteristic of a molding process such as extrusion molding, compression molding, bladder molding, or the like. For example, extrusion molding can be used to form a heat-shrinkable tube that forms the balloon protector 110 over the balloon catheter 120 when heated. Extrusion molding can also be used to form tubular sections of the balloon protector 110 (e.g., the balloon-covering section 112 and the shaft-covering section 114 of the balloon protector 110) while compression molding can be used to form the conical sections of the balloon protector 110 (e.g., the flared section 111 and the transitional section 113 of the balloon protector 110). The tubular sections and the conical sections can be subsequently joined by sintering, solvent bonding, or the like to form the balloon protector 110. In an alternative example, compression molding can be used to form complementary halves, or preforms, of the balloon protector 110, which can be subsequently joined by bladder molding, sintering, solvent bonding, or the like to form the balloon protector 110.

Figure 3A:
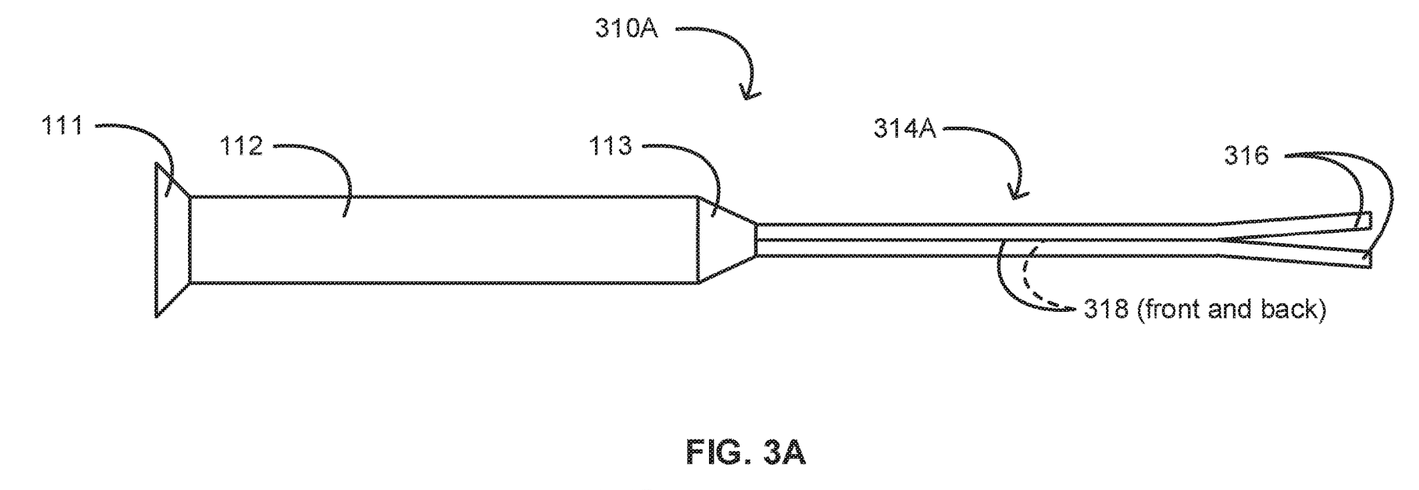
FIG. 3A illustrates a balloon protector including a first peeling mechanism for peeling the shaft-covering section of the balloon protector away from a shaft of a balloon catheter in accordance with some embodiments.

FIG. 3A illustrates a balloon protector 310A including a first separating or peeling mechanism for separating or peeling a shaft-covering section 314A of the balloon protector 310A away from the shaft 122 of the balloon catheter 120 in accordance with some embodiments.

As shown, the first peeling mechanism of the balloon protector 310A includes two or more pull tabs 316 of a proximal end portion of the balloon protector 310A and a commensurate number of weakened areas 318 extending along a length of the shaft-covering section 314A of the balloon protector 310A. The pull tabs 316 are configured to provide a starting point from which to peel the shaft-covering section 314A of the balloon protector 310A away from the shaft 122 of the balloon catheter 120. The weakened areas 318 are configured to facilitate peeling from the starting point of the shaft-covering section 314A provided by the pull tabs 316 through the shaft-covering section 314A up to the transitional section 113 of the balloon protector 310A. The weakened areas 318 can be perforations, scores, or molded grooves.

Figure 3B:
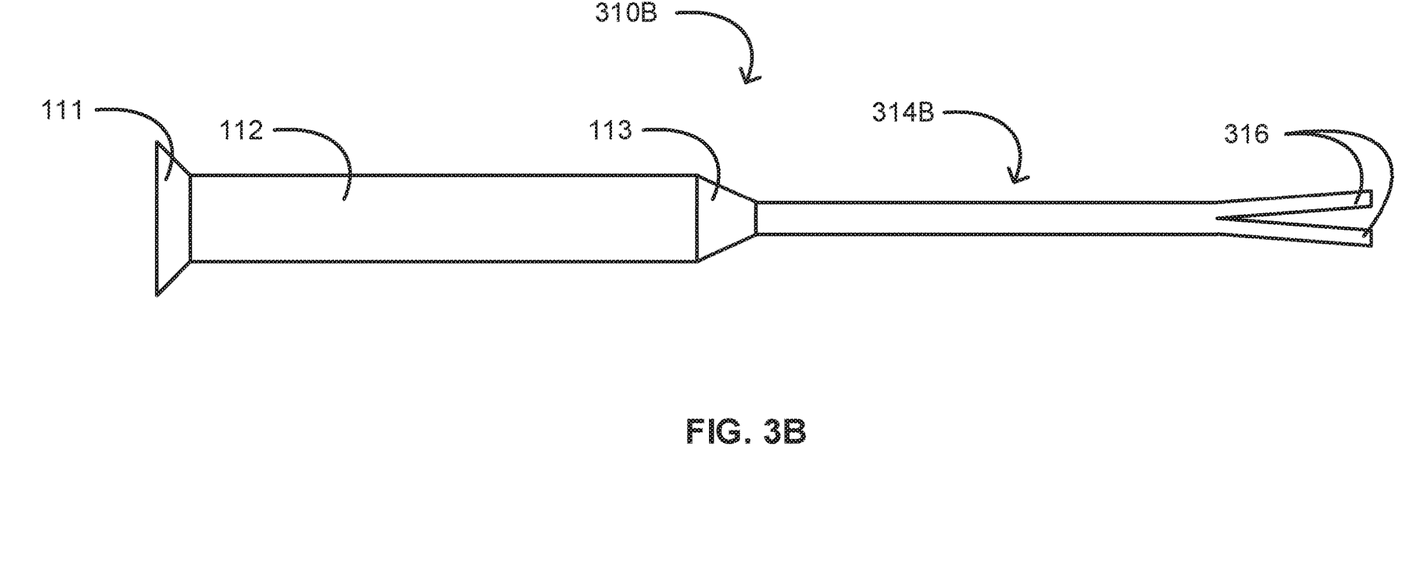
FIG. 3B illustrates a balloon protector including a second peeling mechanism for peeling the shaft-covering section of the balloon protector away from a shaft of a balloon catheter in accordance with some embodiments.

FIG. 3B illustrates a balloon protector 310B including a second separating or peeling mechanism for separating or peeling the shaft-covering section 314B of the balloon protector 310B away from the shaft 122 of the balloon catheter 120 in accordance with some embodiments.

As shown, the second peeling mechanism of the balloon protector 310B includes the same two or more pull tabs 316 of the proximal end portion of the balloon protector 310A; however, the balloon protector 310B does not include the two or more weakened areas 318 extending along the length of the shaft-covering section 314A of the balloon protector 310A. Instead, the balloon protector 310B is formed of a polymeric material in which main chains of the polymeric material are oriented along a length of the shaft-covering section 314B of the balloon protector 310B in an amount sufficient for peeling the shaft-covering section 314B away from the shaft 122 of the balloon catheter 120 along the length of the shaft-covering section 314B without transverse tearing of the shaft-covering section 314B. The main chains of the polymeric material are configured to facilitate peeling from the starting point of the shaft-covering section 314B provided by the pull tabs 316 through the shaft-covering section 314B up to the transitional section 113 of the balloon protector 310B. The polymeric material can be ePTFE.

Figure 3C:
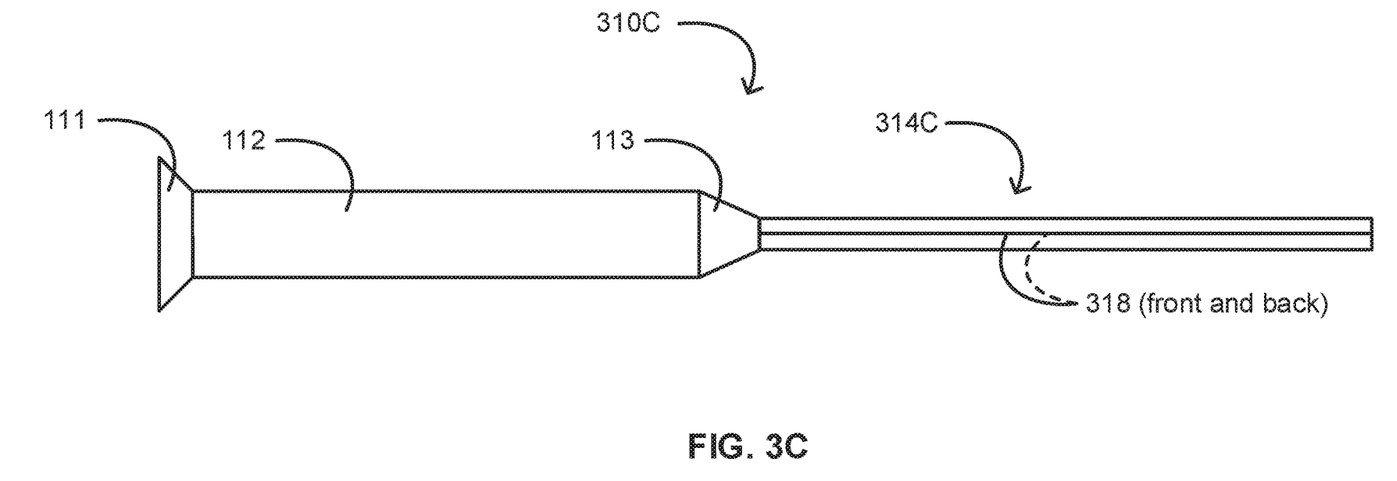
FIG. 3C illustrates a balloon protector including a third peeling mechanism for peeling the shaft-covering section of the balloon protector away from a shaft of a balloon catheter in accordance with some embodiments.

FIG. 3C illustrates a balloon protector 310C including a third separating or peeling mechanism for separating or peeling the shaft-covering section 314C of the balloon protector 110 away from the shaft 122 of the balloon catheter 120 in accordance with some embodiments.

As shown, the third peeling mechanism of the balloon protector 310C includes the same two or more weakened areas 318 extending along the length of the shaft-covering section 314A of the balloon protector 310A; however, the balloon protector 310C does not include the two or more pull tabs 316 of the proximal end portion of the balloon protector 310A. That is, the balloon protector 310C is tabless compared to the balloon protector 310A or 310B. Instead of the pull tabs 316, the proximal end portion of the balloon protector 310C is configured for pinching two opposing proximal end portions of the balloon protector 310C and pulling at least one proximal end portion of the two opposing proximal end portions away from the shaft 122 of the balloon catheter 120 to form instant pull tabs like the pull tabs 316. While not shown, the proximal end portion of the balloon protector 310C can be flared to assist in pinching and pulling the two opposing proximal end portions of the balloon protector 310C to form the instant pull tabs from the proximal end portion of the balloon protector 310C. The weakened areas 318 are configured to facilitate peeling from the starting point of the shaft-covering section 314A provided by the instant pull tabs through the shaft-covering section 314C up to the transitional section 113 of the balloon protector 310C. The weakened areas 318 can be perforations, scores, or molded grooves.

Figure 3D:
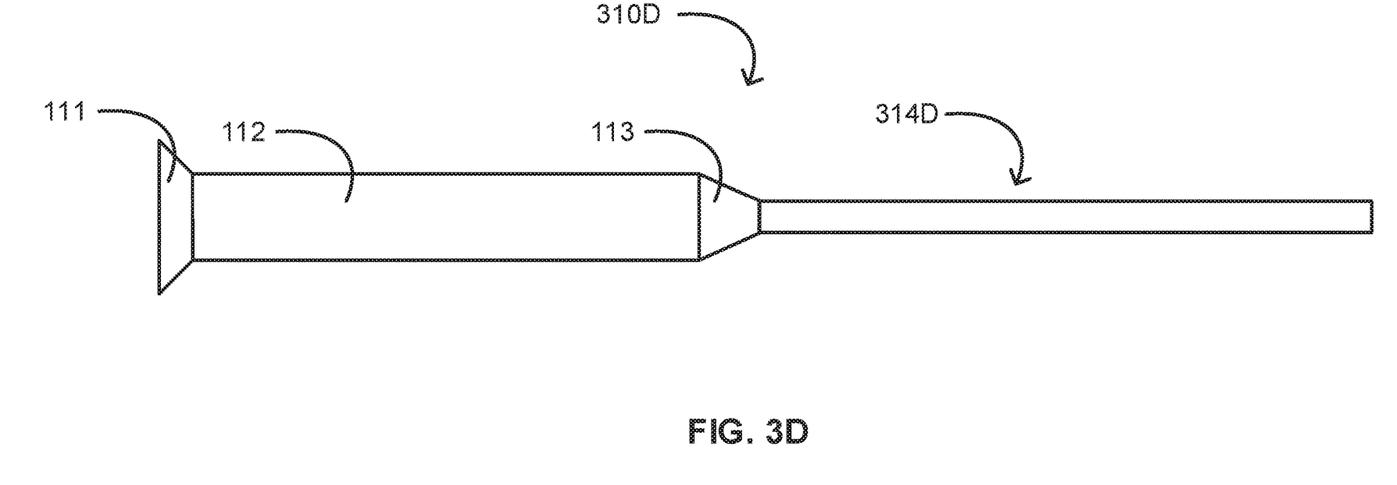
FIG. 3D illustrates a balloon protector including a fourth peeling mechanism for peeling the shaft-covering section of the balloon protector away from a shaft of a balloon catheter in accordance with some embodiments.

FIG. 3D illustrates a balloon protector 310D including a fourth separating or peeling mechanism for separating or peeling the shaft-covering section 314D of the balloon protector 310D away from the shaft 122 of the balloon catheter 120 in accordance with some embodiments.

As shown, the fourth peeling mechanism of the balloon protector 310D does not include the two or more pull tabs 316 of the proximal end portion of the balloon protector 310A or the two or more weakened areas 318 extending along the length of the shaft-covering section 314A of the balloon protector 310A. That is, the balloon protector 310D is tabless compared to the balloon protector 310A or 310B, and the balloon protector 310D lacks weakened areas compared to the balloon protector 310A or 310C. Instead of the pull tabs 316, the proximal end portion of the balloon protector 310D is configured for pinching two opposing proximal end portions of the balloon protector 310D and pulling at least one proximal end portion of the two opposing proximal end portions away from the shaft 122 of the balloon catheter 120 to form instant pull tabs like the pull tabs 316. While not shown, the proximal end portion of the balloon protector 310D can be flared to assist in pinching and pulling the two opposing proximal end portions of the balloon protector 310D to form the instant pull tabs from the proximal end portion of the balloon protector 310D. Instead of the weakened areas 318, the balloon protector 310D is formed of a polymeric material in which main chains of the polymeric material are oriented along a length of the shaft-covering section 314D of the balloon protector 310D in an amount sufficient for peeling the shaft-covering section 314D away from the shaft 122 of the balloon catheter 120 along the length of the shaft-covering section 314D without transverse tearing of the shaft-covering section 314D. The main chains of the polymeric material are configured to facilitate peeling from the starting point of the shaft-covering section 314D provided by the instant pull tabs through the shaft-covering section 314D up to the transitional section 113 of the balloon protector 310D. The polymeric material can be ePTFE.

Methods

FIGS. 4A-4E and 5 illustrate a number of steps in a method of the catheter assembly 100 in accordance with some embodiments. While the catheter assembly 100 of FIGS. 4A-4E is shown with the balloon 124 of the balloon catheter 120 in an exaggerated state to emphasize a difference in diameter from a shaft 122 of the balloon catheter 120, it should be understood that the catheter assembly 100 is typically provided with the balloon 124 in an uninflated state, and, during the method of the catheter assembly 100, the balloon 124 is inflated after insertion into a patient and deflated prior to withdrawal from the patient.

Figure 4A:
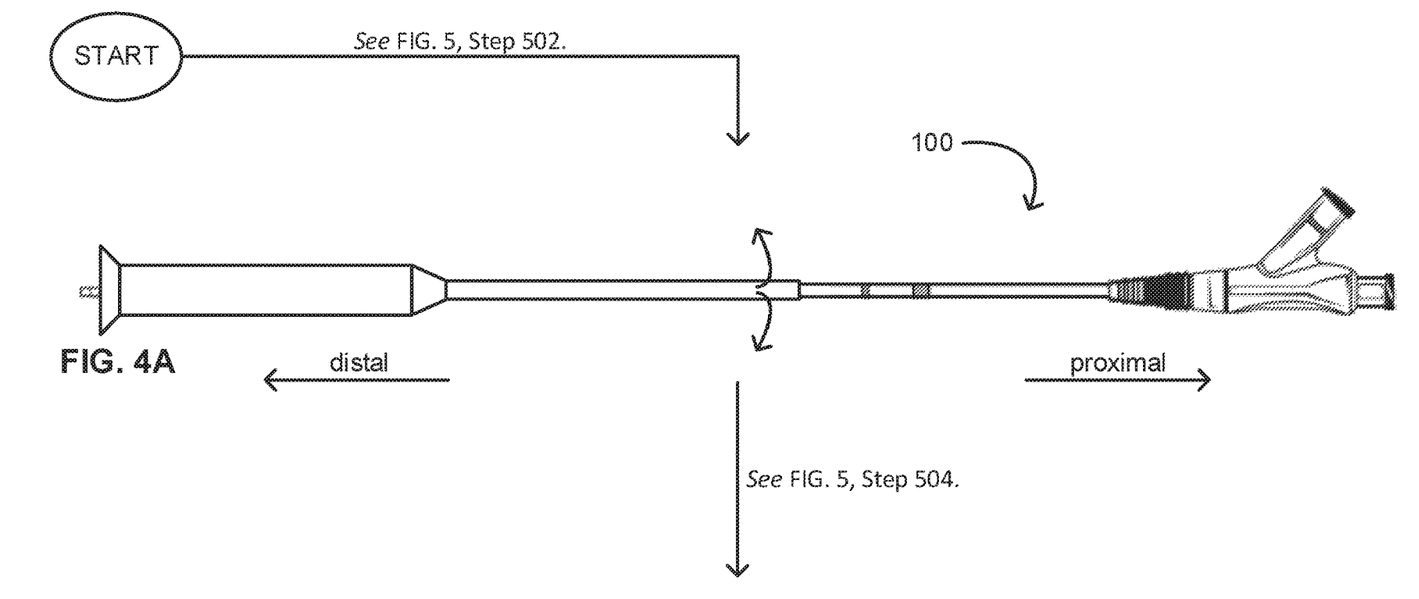
FIG. 4A illustrates a step in a method of a catheter assembly of peeling the shaft-covering section of the balloon protector away from the shaft of the balloon catheter in accordance with some embodiments.
Figure 4B:
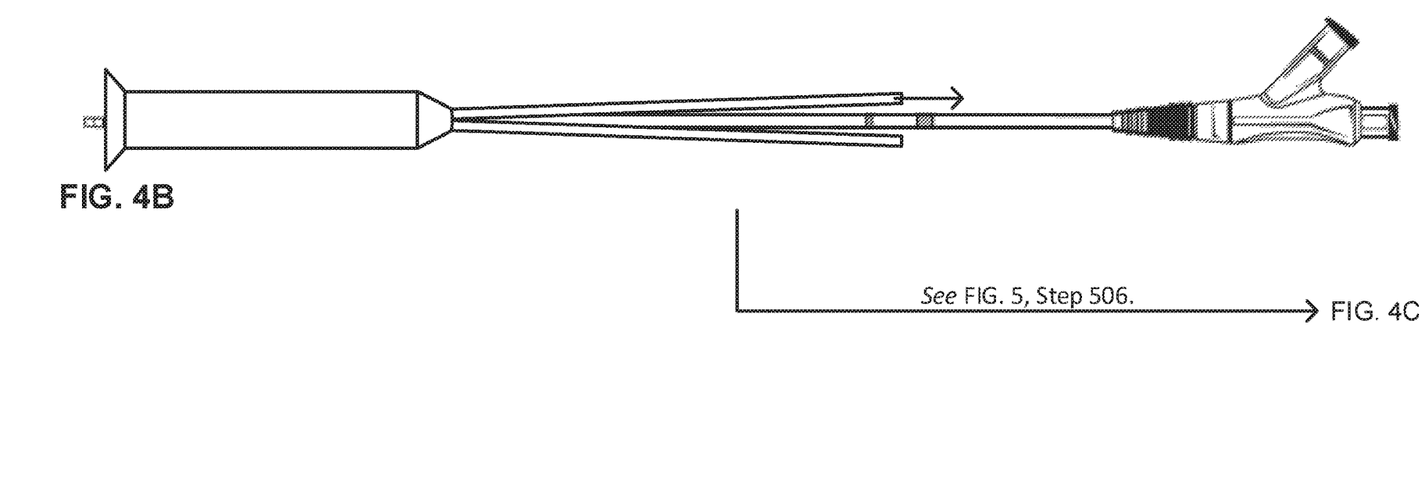
FIG. 4B illustrates a step in the method of the catheter assembly of sliding the balloon-covering section of the balloon protector off the balloon of the balloon catheter in accordance with some embodiments.

FIG. 4A illustrates a step in the method of the catheter assembly 100 of separating or peeling the shaft-covering section 114 of the balloon protector 110 away from the shaft 122 of the balloon catheter 120 in accordance with some embodiments. FIG. 4B illustrates a step in the method of the catheter assembly 100 of sliding the balloon-covering section 112 of the balloon protector 110 off the balloon 124 of the balloon catheter 120 in accordance with some embodiments.

Figure 5:
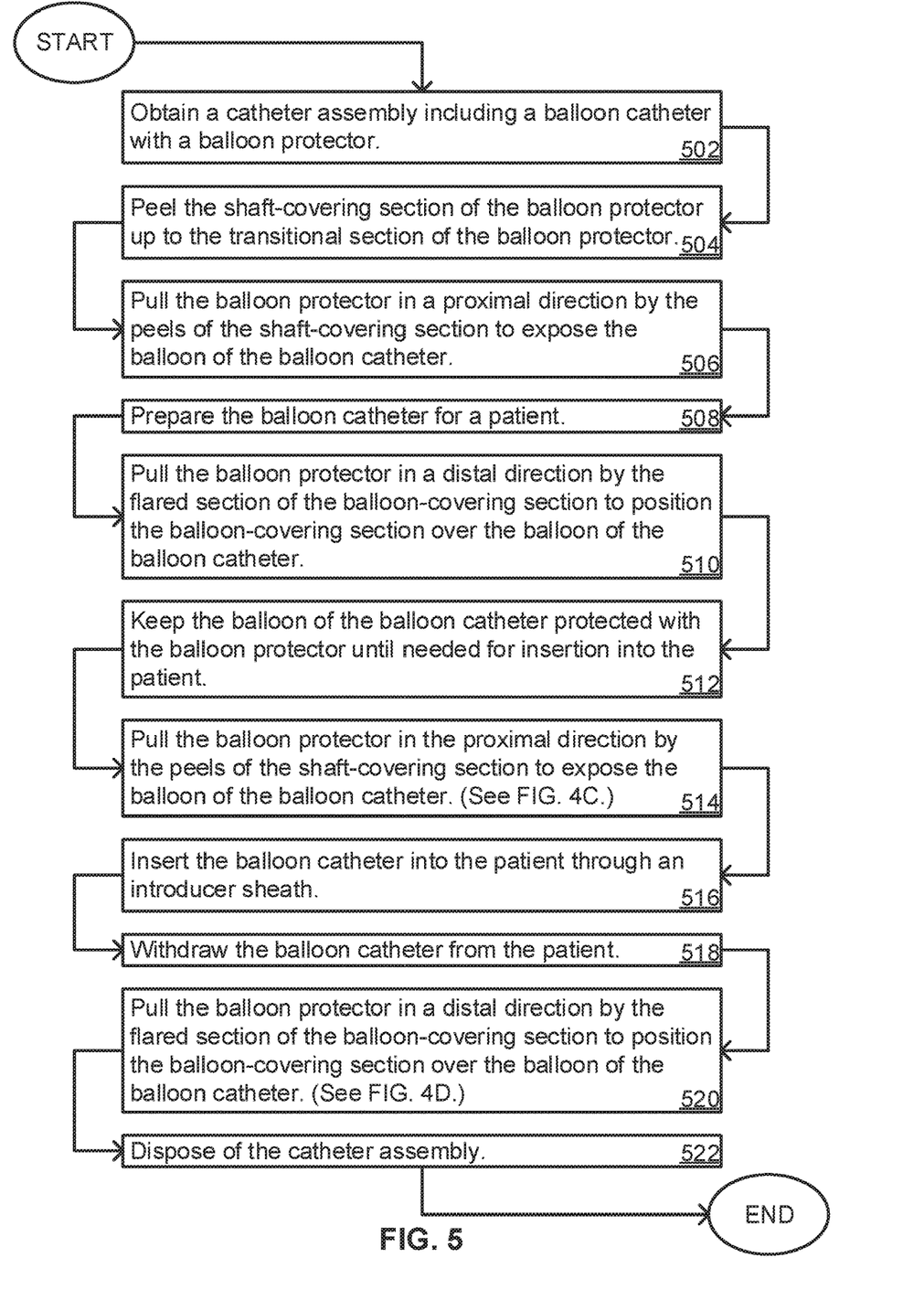
FIG. 5 illustrates the steps of the method of the catheter assembly of FIGS. 4A-4E.

As shown, the method of the catheter assembly 100 includes a step 502 of obtaining the catheter assembly 100. The catheter assembly 100 includes the balloon catheter 120 and the balloon protector 110. The shaft-covering section 114 of the balloon protector 110 has a sliding or location clearance fit over the shaft 122 of the balloon catheter 120, and the balloon-covering section 112 of the balloon protector 110 has a running clearance fit over the balloon 124 of the balloon catheter 120.

The method further includes a step 504 of separating or peeling the shaft-covering section 114 of the balloon protector 110 away from the shaft 122 of the balloon catheter 120. Peeling the shaft-covering section 114 of the balloon protector 110 includes peeling the shaft-covering section 114 in a direction toward a distal end of the balloon catheter 120 up to the transitional section 113 of the balloon protector 110. When pull tabs are present (e.g., the two or more pull tabs 316 of balloon protector 310A or 310 B), peeling the shaft-covering section 114 of the balloon protector 110 further includes grasping two pull tabs of the proximal end portion of the balloon protector 110 and pulling at least one pull tab of the two pull tabs away from the shaft 122 of the balloon catheter 120. Alternatively, peeling the shaft-covering section 114 of the balloon protector 110 further includes grasping the two pull tabs of the proximal end portion of the balloon protector 110 and pulling the pull tabs in opposing directions to peel the shaft-covering section 114 of the balloon protector 110 away from the shaft 122 of the balloon catheter 120. When pull tabs are not present, peeling the shaft-covering section 114 of the balloon protector 110 further includes pinching two opposing proximal end portions of the balloon protector 110 and pulling at least one proximal end portion of the two opposing proximal end portions away from the shaft 122 of the balloon catheter 120. Alternatively, peeling the shaft-covering section 114 of the balloon protector 110 further includes pinching two opposing proximal end portions of the balloon protector 110 and pulling the proximal end portions of the balloon protector 110 in opposing directions to peel the shaft-covering section 114 of the balloon protector 110 away from the shaft 122 of the balloon catheter 120.

Figure 4C:
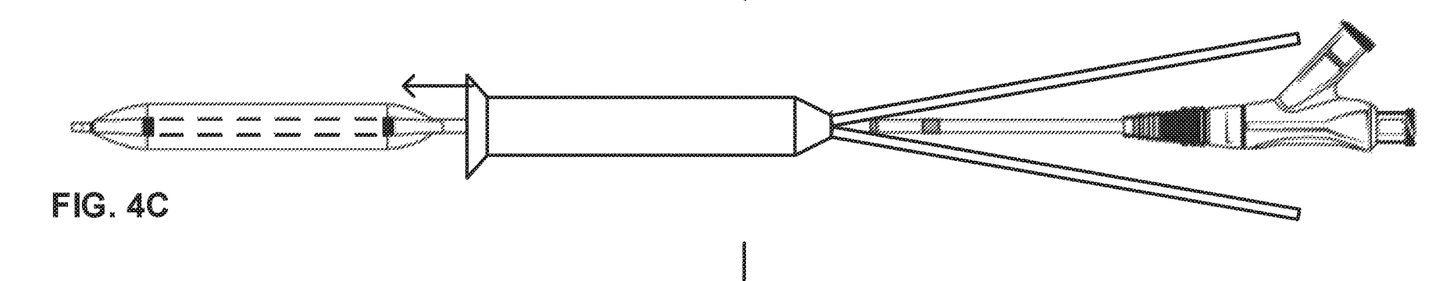
FIG. 4C illustrates a step in the method of the catheter assembly of sliding the balloon-covering section of the balloon protector back over the balloon of the balloon catheter in accordance with some embodiments.

The method further includes a step 506 of translating or sliding the balloon-covering section 112 of the balloon protector 110 off the balloon 124 of the balloon catheter 120 after the shaft-covering section 114 of the balloon protector 110 is peeled away from the shaft 122 of the balloon catheter 120. Sliding the balloon-covering section 112 of the balloon protector 110 from a first position over the balloon 124 of the balloon catheter 120 to a second position off the balloon 124 includes sliding the balloon-covering section 112 in a direction toward a proximal end of the balloon catheter 120. Sliding the balloon-covering section 112 in the direction toward the proximal end of the balloon catheter 120 can be accomplished by pulling the balloon protector 110 by peels formed in the shaft-covering section 114 of the balloon protector 110 by peeling the shaft-covering section 114. However, sliding the balloon-covering section 112 of the balloon protector 110 off the balloon 124 of the balloon catheter 120 need not be completely off the balloon 124 as shown in FIG. 4C. Indeed, the balloon-covering section 112 of the balloon protector 110 need only be slid off as much of the balloon 124 of the balloon catheter 120 as a clinician deems necessary for preparing the balloon catheter 120 in accordance with a step 508 for insertion into a patient. For example, the clinician might only need to see a portion of the balloon 124 to make sure it inflates properly when preparing the balloon catheter 120 for insertion into the patient, which might require sliding the balloon protector 110 off just a portion of the balloon 124, particularly when the inner diameter of the balloon-covering section 112 of the balloon protector 110 is configured to accommodate the balloon 124 of the balloon catheter 120 in the inflated state. And, for example, the clinician might not need to see any portion of the balloon 124 while priming the guide wire lumen of the balloon catheter 120 when preparing the balloon catheter 120 for insertion into the patient.

FIG. 4C illustrates a step in the method of the catheter assembly of sliding the balloon-covering section 112 of the balloon protector 110 back over the balloon 124 of the balloon catheter 120 in accordance with some embodiments.

As shown, the method further includes a step 510 of sliding the balloon-covering section 112 of the balloon protector 110 back over the balloon 124 of the balloon catheter 120 after preparing the balloon catheter 120 for insertion into the patient—if the balloon protector 110 was slid off the balloon 124 in the previous step. Sliding the balloon-covering section 112 of the balloon protector 110 back over the balloon 124 of the balloon catheter 120 protects the balloon 124 in accordance with a step 512 until the balloon catheter 120 is inserted into the patient. Sliding the balloon-covering section 112 of the balloon protector 110 back over the balloon 124 of the balloon catheter 120 can be accomplished by either pulling the balloon protector 110 in the direction toward the distal end of the balloon catheter 120 by the circumferential tab formed of the flared section 111 of the balloon protector 110 or pushing the balloon protector 110 toward the distal end of the balloon catheter 120 by the transitional section 113 of the balloon protector 110 to position the balloon-covering section 112 over the balloon 124.

Figure 4D:
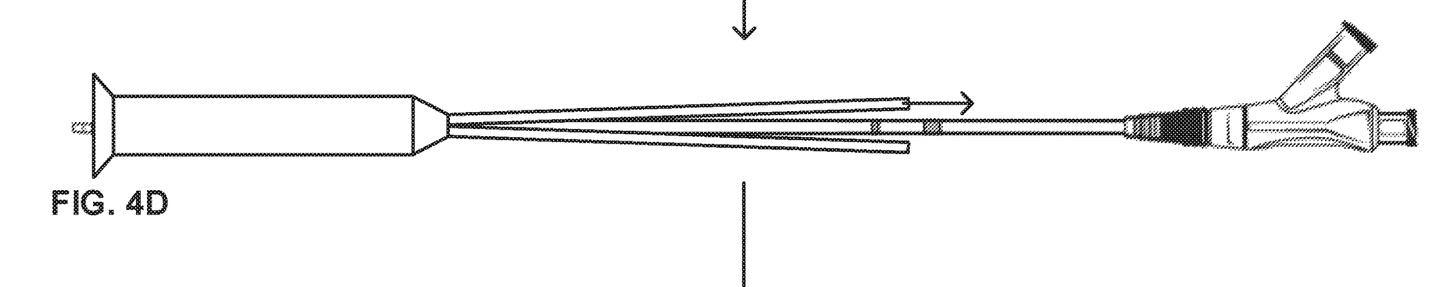
FIG. 4D illustrates a step in the method of the catheter assembly of sliding the balloon-covering section of the balloon protector off the balloon of the balloon catheter in accordance with some embodiments.

FIG. 4D illustrates a step in the method of the catheter assembly of sliding the balloon-covering section 112 of the balloon protector 110 off the balloon 124 of the balloon catheter 120 in accordance with some embodiments.

As shown, the method further includes a step 514 of sliding the balloon-covering section 112 of the balloon protector 110 off the balloon 124 of the balloon catheter 120 after the shaft-covering section 114 of the balloon protector 110 is peeled away from the shaft 122 of the balloon catheter 120 and just before inserting the balloon catheter 120 into the patient by way of an introducer sheath in accordance with a step 516. Again, sliding the balloon-covering section 112 of the balloon protector 110 off the balloon 124 of the balloon catheter 120 includes sliding the balloon-covering section 112 in the direction toward the proximal end of the balloon catheter 120. Sliding the balloon-covering section 112 in the direction toward the proximal end of the balloon catheter 120 can be accomplished by pulling the balloon protector 110 by the peels formed in the shaft-covering section 114 of the balloon protector 110 by peeling the shaft-covering section 114. However, sliding the balloon-covering section 112 of the balloon protector 110 off the balloon 124 of the balloon catheter 120 need not be completely off the balloon 124. Indeed, the balloon-covering section 112 of the balloon protector 110 need only be slid off as much of the balloon 124 of the balloon catheter 120 as the clinician deems necessary for inserting the balloon catheter 120 into the introducer sheath. This is because the flared section 111 of the distal end portion of the balloon protector 110 can be used to cup a proximal end portion of the introducer sheath, and—due to the running clearance fit of the balloon-covering section 112 of the balloon protector 110 over the balloon 124 of the balloon catheter 120—the proximal end portion of the introducer sheath can be used to slide the balloon-covering section 112 off the balloon 124 as the balloon catheter 120 is inserted into the patient. An advantage of sliding the balloon-covering section 112 of the balloon protector 110 off the balloon 124 of the balloon catheter 120 while inserting the balloon catheter 120 into the introducer sheath is that the clinician never has to handle the balloon catheter 120 by the balloon 120. Not touching the drug coating on the balloon 124 of the balloon catheter 120 keeps the drug coating dry and free from contamination.

Figures 4D, 4E:
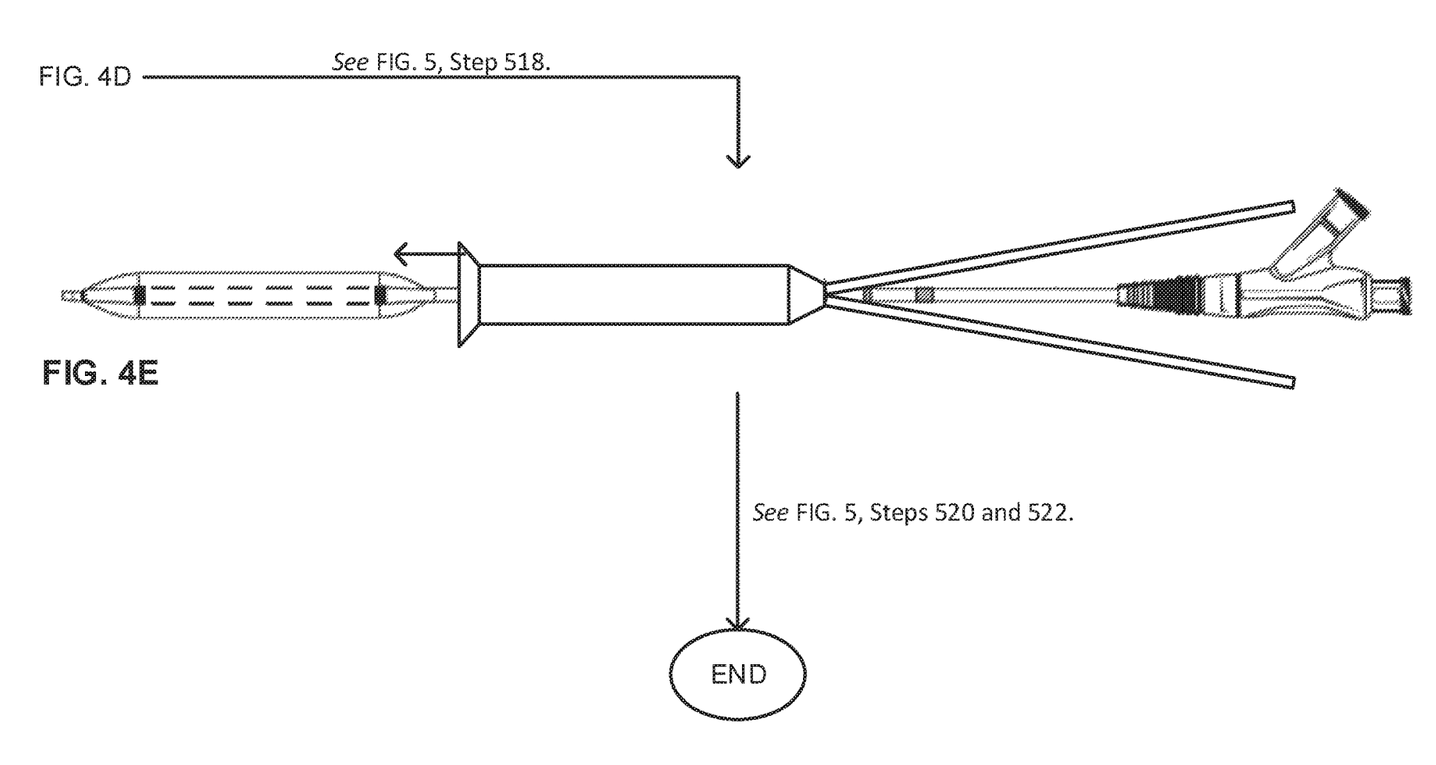
FIG. 4E illustrates a step in the method of the catheter assembly of sliding the balloon-covering section of the balloon protector back over the balloon of the balloon catheter in accordance with some embodiments.

FIG. 4E illustrates a step in the method of the catheter assembly of sliding the balloon-covering section 112 of the balloon protector 110 back over the balloon 124 of the balloon catheter 120 in accordance with some embodiments.

As shown, the method further includes a step 520 of sliding the balloon-covering section 112 of the balloon protector 110 back over the balloon 124 of the balloon catheter 120 after withdrawing the balloon catheter 120 from the patient in accordance with a step 518. Sliding the balloon-covering section 112 of the balloon protector 110 back over the balloon 124 of the balloon catheter 120 protects clinicians and others from inadvertently coming into contact with any residual anti-proliferative drug on the balloon 124 when handling the balloon catheter 120 after use on the patient. Again, sliding the balloon-covering section 112 of the balloon protector 110 back over the balloon 124 of the balloon catheter 120 can be accomplished by either pulling the balloon protector 110 in the direction toward the distal end of the balloon catheter 120 by the circumferential tab formed of the flared section 111 of the balloon protector 110 or pushing the balloon protector 110 toward the distal end of the balloon catheter 120 by the transitional section 113 of the balloon protector 110 to position the balloon-covering section 112 over the balloon 124.

The method further includes a step 522 of disposing of the catheter assembly 100 after sliding the balloon-covering section 112 of the balloon protector 110 back over the balloon 124 of the balloon catheter 120. Disposing of the catheter assembly 100 in this configuration protects clinicians and others from inadvertently coming into contact with any residual anti-proliferative drug on the balloon 124 when handling the balloon catheter 120 after use on the patient.

These and other features of the concepts provided herein will become more apparent to those of skill in the art in view of the accompanying drawings and following description, which disclose particular embodiments of such concepts in greater detail.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A balloon protector for use with a balloon catheter, the balloon catheter including a shaft and a drug-coated balloon, the balloon protector comprising:
    a balloon-covering section configured to cover the drug-coated balloon with a running clearance fit; and
    a shaft-covering section coupled to the balloon-covering section, the shaft-covering section configured to contact at least a portion of the shaft in a sliding or location clearance fit, wherein the shaft-covering section is configured to separate from the shaft without separating from the balloon-covering section to permit translation of the balloon-covering section from a first position over the drug-coated balloon to a second position over the shaft after the shaft-covering section is separated from the shaft; and
    a transitional section coupling a smaller diameter of the shaft-covering section to a larger diameter of the balloon-covering section, the transitional section configured to cover a proximal shoulder of the drug-coated balloon in the first position.

2. The balloon protector according to claim 1, wherein the balloon-covering section includes a flared section configured to cover a distal shoulder of the drug-coated balloon in the first position, the flared section including a circumferential tab configured to facilitate translation of the balloon protector relative to the balloon catheter.

3. The balloon protector according to claim 1, wherein the shaft-covering section includes two or more pull tabs configured to facilitate separation of the shaft-covering section from the shaft.

4. The balloon protector according to claim 3, wherein the shaft-covering section includes two or more weakened areas aligned with the two or more pull tabs, the two or more weakened areas selected from the group consisting of perforations, scores, molded grooves, and combinations thereof.

5. The balloon protector according to claim 1, wherein the balloon-covering section and the shaft-covering section are formed of expanded polytetrafluoroethylene or high-density polyethylene.

6. A catheter assembly, comprising:
    a balloon catheter including a shaft and an anti-proliferative drug-coated balloon in an uninflated state disposed about a distal end portion of the shaft; and
    a balloon protector including:
        a balloon-covering section configured to cover the anti-proliferative drug-coated balloon with a running clearance fit;
        a shaft-covering section coupled to the balloon-covering section, the shaft-covering section configured to contact at least a portion of the shaft in a sliding or location clearance fit; and a transitional section coupling a smaller diameter of the shaft-covering section to a larger diameter of the balloon-covering section, the transitional section configured to cover a proximal shoulder of the anti-proliferative drug-coated balloon in a first position, wherein the shaft-covering section is configured to separate from the shaft without separating from the balloon-covering section to permit translation of the balloon-covering section from the first position over the anti-proliferative drug-coated balloon to a second position over the shaft after the shaft-covering section is separated from the shaft.

7. The catheter assembly according to claim 6, wherein the balloon-covering section includes a flared section configured to cover a distal shoulder of the anti-proliferative drug-coated balloon in the first position, the flared section including a circumferential tab configured to facilitate translation of the balloon protector relative to the balloon catheter.

8. The catheter assembly according to claim 6, wherein the shaft-covering section includes two or more pull tabs configured to facilitate separation of the shaft-covering section from the shaft.

9. The catheter assembly according to claim 8, wherein the shaft-covering section includes two or more weakened areas aligned with the two or more pull tabs, the two or more weakened areas selected from the group consisting of perforations, scores, molded grooves, and combinations thereof.

10. The catheter assembly according to claim 8, wherein the shaft-covering section is formed of a polymeric material in which main chains of the polymeric material are oriented along a length of the shaft-covering section in an amount sufficient for separating the shaft-covering section from the shaft.

11. A method of a catheter assembly, comprising:

separating a shaft-covering section of a balloon protector from a shaft of a balloon catheter, the shaft-covering section configured to contact at least a portion of the shaft in a sliding or location clearance fit, the separating including peeling the shaft-covering section up to a transitional section coupling a smaller diameter of the shaft-covering section to a larger diameter of a balloon-covering section, the transitional section configured to cover a proximal shoulder of a drug-coated balloon of the balloon catheter in a first position; and after separating the shaft-covering section from the shaft, translating the balloon-covering section from the first position in which the balloon-covering section has a running clearance fit over the drug-coated balloon to a second position over the shaft without separating the balloon-covering section from the shaft-covering section.

12. The method according to claim 11, wherein:

separating the shaft-covering section from the shaft includes peeling the shaft-covering section in a direction toward a distal end of the balloon catheter, and translating the balloon-covering section from the first position to the second position includes sliding the balloon-covering section in a direction toward a proximal end of the balloon catheter.

13. The method according to claim 11, wherein separating the shaft-covering section from the shaft includes grasping two pull tabs of the shaft-covering section and pulling at least one pull tab of the two pull tabs away from the shaft.

14. The method according to claim 11, further comprising:

translating the balloon-covering section from the second position to the first position; and preparing the balloon catheter for insertion into a patient, wherein translating the balloon-covering section from the second position to the first position protects the drug-coated balloon while preparing the balloon catheter for insertion into the patient.

15. The method according to claim 11, further comprising:

translating the balloon-covering section from the second position to the first position after withdrawing the balloon catheter from a patient, wherein translating the balloon-covering section from the second position to the first position protects clinicians and others from inadvertently coming into contact with any residual anti-proliferative drug on the drug-coated balloon when handling the balloon catheter after use on the patient.

16. The method according to claim 15, wherein translating the balloon-covering section from the second position to the first position includes pulling the balloon protector in a direction toward a distal end of the balloon catheter by a circumferential tab formed of a flared section of the balloon-covering section.

* * * * *